United States Patent [19]
Sato et al.

[11] Patent Number: 5,189,211
[45] Date of Patent: Feb. 23, 1993

[54] SULFONAMIDE DERIVATIVES

[75] Inventors: Masakazu Sato, Konosu; Yutaka Kawashima, Tatebayashi; Jun Goto, Omiya; Yoshiyuki Chiba; Mikio Satake, both of Hachioji; Chuzo Iwata, Settsu; Takeshi Imanishi, Nara, all of Japan

[73] Assignees: Taisho Pharmaceutical Co., Ltd.; Nippon Suisan Kaisha, Ltd., both of Japan

[21] Appl. No.: 736,616

[22] Filed: Jul. 26, 1991

[30] Foreign Application Priority Data

Aug. 1, 1990 [JP] Japan .................. 2-204732

[51] Int. Cl.$^5$ ............... C07C 317/14; C07C 317/26; C07C 317/48
[52] U.S. Cl. ..................... 562/430; 546/293; 560/10; 560/12; 560/13; 562/427; 564/86; 564/87; 564/89; 564/92
[58] Field of Search ............ 562/430; 560/12, 13; 546/293; 564/92

[56] References Cited

U.S. PATENT DOCUMENTS

| | | | |
|---|---|---|---|
| 4,258,058 | 3/1981 | Witte et al. | 424/309 |
| 4,443,477 | 4/1984 | Witte et al. | 424/319 |
| 4,717,736 | 6/1988 | Rokach et al. | 514/562 |
| 4,948,809 | 8/1990 | Witte et al. | 514/538 |
| 4,981,873 | 1/1991 | Witte et al. | 514/562 |

*Primary Examiner*—Paul J. Killos
*Assistant Examiner*—B. Frazier
*Attorney, Agent, or Firm*—Lorusso & Loud

[57] ABSTRACT

A sulfonamide derivative represented by the Formula:

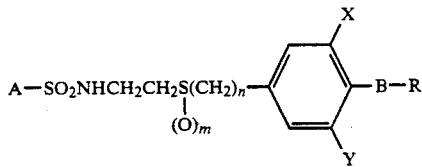

wherein A, B, X, Y, R, m and n are as defined in the specification, and a salt thereof have thromboxane $A_2$ antagonism, therefore they are useful, for example, as blood platelet aggregation inhibiting agents.

3 Claims, No Drawings

SULFONAMIDE DERIVATIVES

BACKGROUND OF THE INVENTION (1) Field of the Invention

The present invention relates to sulfonamide derivatives, and more particularly to novel sulfonamide derivatives having thromboxane $A_2$ antagonism and intermediates for the preparation thereof.

(2) Prior Art

Some sulfonamide derivatives having thromboxane antagonism have been known in U.S. Pat. No. 4,258,058, but the action is insufficient.

As a result of the earnest research, the present inventors have found novel sulfonamide derivatives having thromboxane $A_2$ antagonism, and have accomplished the present invention.

SUMMARY OF THE INVENTION

An object of the present invention is to provide a sulfonamide derivative represented by the following Formula I:

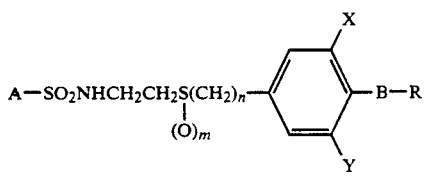

wherein A is a naphthyl group, a pyridyl group, a phenyl group, a phenyl group substituted by 1 to 5 members selected from the group consisting of a halogen atom, an alkyl group having 1 to 4 carbon atoms, an alkoxy group having 1 to 4 carbon atoms, a nitro group and an acetamido group, or an alkyl group having 1 to 20 carbon atoms, B is an alkylene group having 1 to 3 carbon atoms, a group of —OCH$_2$— or a group of —CH=CH—, X and Y are the same or different, and are each a hydrogen atom or a fluorine atom, R is a carboxy group, an alkyoxycarbonyl group having 2 to 5 carbon atoms, a hydroxymethyl group or a group of

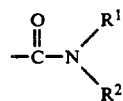

(wherein R$^1$ is a hydrogen atom or an alkyl group having 1 to 3 carbon atoms, and R$^2$ is a hydrogen atom, a hydroxyl group, an alkyl group having 1 to 3 carbon atoms, a carboxymethyl group or an alkoxycarbonylmethyl group having 3 to 6 carbon atoms), m is an integer from 0 to 2, n is an integer from 0 to 3, or a salt thereof.

Another object of the present invention is to provide a thiophenol derivative represented by the following Formula I':

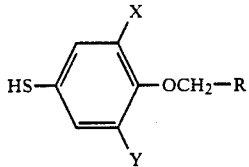

wherein X and Y are the same or different, and each a hydrogen atom or a fluorine atom, R is a carboxy group, an alkoxycarbonyl group having 2 to 5 carbon atoms, a hydroxymethyl group or a group of

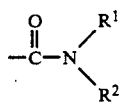

(wherein R$^1$ is a hydrogen atom or an alkyl group having 1 to 3 carbon atoms, and R$^2$ is a hydrogen atom, a hydroxyl group, an alkyl group having 1 to 3 carbon atoms, a carboxymethyl group or an alkoxycarbonylmethyl group having 3 to 6 carbon atoms).

DETAILED DESCRIPTION OF THE INVENTION

In the present invention, the alkyl group refers to a straight or branched chain alkyl group such as, for example, a methyl group, an ethyl group, a propyl group, an isopropyl group, a butyl group, an isobutyl group, a pentyl group, an isopentyl group, a hexyl group, an octyl group, a decyl group, a hexadecyl group and an eicosyl group. The alkoxy group refers to a straight or branched chain alkoxy group such as, for example, a methoxy group, an ethoxy group, a propoxy group, an isopropoxy group, a butoxy group and an isobutoxy group. The halogen atom refers to a fluorine atom, a chlorine atom, a bromine atom and an iodine atom. The alkylene group refers to a straight or branched chain alkylene group such as, for example, a methylene group, an ethylene group, a propylene group and a trimethylene group. The alkoxycarbonyl group refers to an alkoxycarbonyl group of which alkoxy moiety is straight or branched, for example, a methoxycarbonyl group, an ethoxycarbonyl group, a propoxycarbonyl group, an isopropoxycarbonyl group, a butoxycarbonyl group and an isobutoxycarbonyl group. The alkoxycarbonylmethyl group refers to those having a straight or branched chain alkoxy group, for example, a methoxycarbonylmethyl group, an ethoxycarbonylmethyl group, a propoxycarbonylmethyl group and an isopropoxycarbonylmethyl group. The salt of the compound of the present invention refers to a pharmaceutically acceptable salt, for example, salts of sodium, potassium, calcium, ammonium and aluminium.

Among preferred compounds of the present invention are compounds of Formula I wherein A is a phenyl group substituted by 1 to 5 members selected from the group consisting of a halogen atom, an alkyl group having 1 to 4 carbon atoms, an alkoxy group having 1 to 4 carbon atoms, a nitro group and an acetamido group, B is an alkylene group having 1 to 3 carbon atoms or a group of —OCH$_2$—, X and Y are the same or different, and are each a hydrogen atom or a fluorine atom, R is a carboxy group or an alkoxycarbonyl group having 2 to 5 carbon atoms, m is an integer of 0 to 2 and n is 0.

Among further preferred compounds are 2,6-difluoro-4-[2-(4-chlorophenylsulfonylamino)ethylthio]phenoxyacetic acid, 2,6-difluoro-4-[2-(4-methylphenylsulfonylamino)ethylthio]phenoxyacetic acid, 4-[2-(4-fluorophenylsulfonylamino)ethylthio]phenylacetic acid, 4-[2-(4-bromophenylsulfonylamino)ethylthio]phenylacetic acid, 4-[2-(4methoxyphenylsulfonylamino)ethylthio]phenylacetic acid, 4-[2-(4-nitrophenylsulfonylamino)ethylthio]phenylacetic acid, 2,6-difluoro-4-[2-(4-fluorophenylsulfonylamino)ethylthio]phenoxyacetic acid, 2,6-difluoro-4-[2-(4-bromophenylsulfonylamino)ethylthio]phenoxyacetic acid, 2,6-difluoro-4-[2-(4-nitrophenylsulfonylamino)ethylthio]phenoxyacetic acid and 2,6-difluoro-4-[2-(4-methoxyphenylsulfonylamino)ethylthio]phenoxyacetic acid.

The compound of Formula I of the present invention can be prepared according to the following methods.

(1) The compound of Formula I wherein n is O, B is —OCH$_2$— can be prepared according to a following reaction scheme (wherein X, Y and R are as defined above, and Hal is a halogen atom).

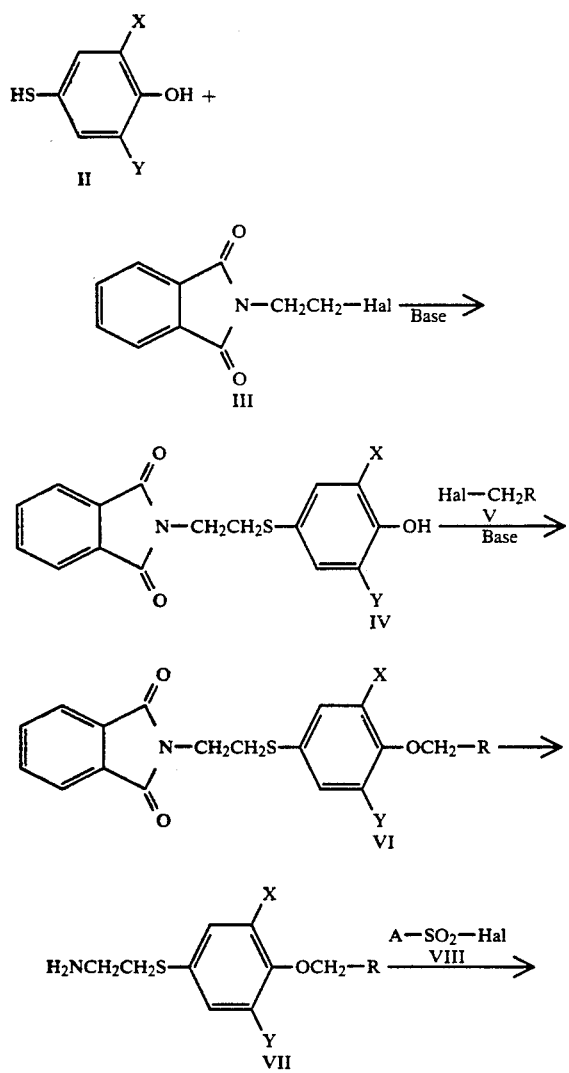

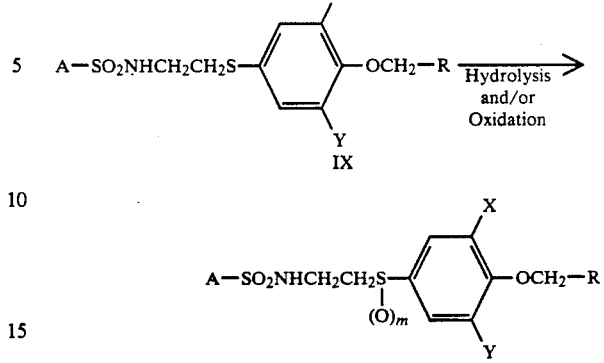

A compound of Formula II (known or prepared by a known manner) is reacted with a compound of Formula III in a solvent in the presence of a base to give a compound of Formula IV. Examples of the base are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). Examples of the solvent are reaction-inert solvents such as N,N-dimethylformamide, dimethyl sulfoxide, acetone, ethanol, isopropanol, methanol, tetrahydrofuran, acetonitrile and water.

Then, a compound of Formula IV is reacted with a compound of Formula V in the presence of a base to give a compound of Formula VI. Examples of the base are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). In this reaction, there can be used a reaction accelerator such as phase-transfer catalysts (e.g. trimethylbenzylammonium chloride) and sodium iodide, and a solvent such as reaction-inert solvents such as methylene chloride, chloroform, N,N-dimethylformamide, dimethyl sulfoxide, acetone, ethanol, isopropanol, methanol, tetrahydrofuran, acetonitrile and water.

The phthalimino group of the compound of Formula VI is eliminated by an ordinary manner, for example, by treating with hydrazine, N-methylhydrazine or N,N'-dimethylhydrazine in the absence or presence of a solvent to give a compound of Formula VII. Examples of the solvent are reaction-inert solvents such as methanol, ethanol, dichloromethane, tetrahydrofuran and chloroform. The compound of Formula VII can be isolated in the form of a salt, e.g. the hydrochloride, or can be used in the solution for the next reaction without any isolation.

The compound of Formula VII is reacted with a compound of Formula VIII in the presence of a base to give a compound of Formula IX. Examples of the base are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). In this reaction, there can be used a solvent, for example, reaction-inert solvents such as dichloromethane, chloroform, tetrahydrofuran and acetonitrile.

A compound of Formula IX can also be converted, by hydrolysis of ester or oxidation of the sulfur atom, into a different compound of the present invention. The hydrolysis of ester can be carried out according to an ordinary manner under the alkali condition (e.g. by using sodium hydroxide and potassium hydroxide) and the oxidation of the sulfur atom can be carried out according to an usual manner (e.g. by using hydrogen peroxide or m-chloroperbenzoic acid).

The compound of Formula II wherein X=Y=a fluorine atom, or X=a hydrogen atom and Y=a fluorine atom, can be synthesized by being subjected to sulfonation of 2,6-difluorophenol or 2-fluorophenol by a known sulfonation method (e.g. by using chlorosulfonic acid), halogenation in order to introduce a halosulfonyl group, and reduction by an ordinary reduction (e.g. by using tin or zinc under acidic conditions).

(2) The compound of Formula I wherein n=O and B is —OCH$_2$— can also be prepared according to the following reaction scheme (wherein X, Y and R are as defined above, and Hal is a halogen atom).

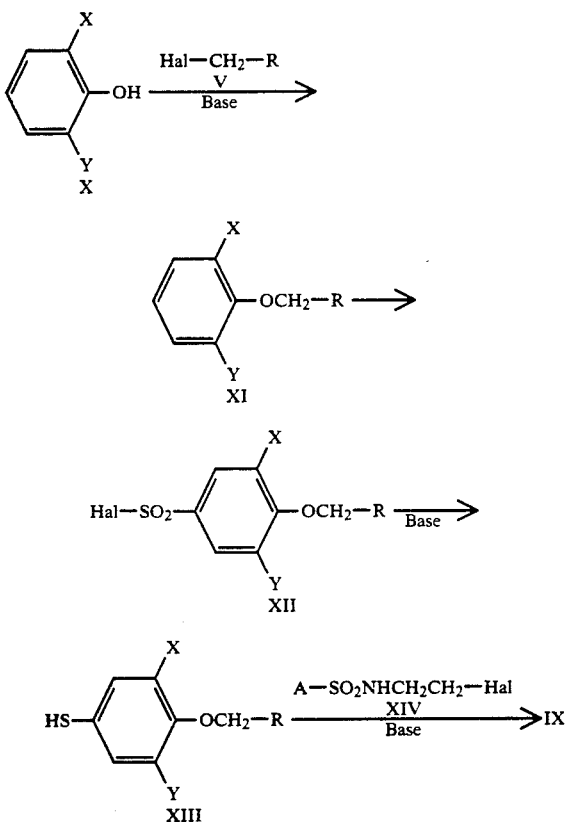

A compound of Formula X is reacted with a compound of Formula V in the presence of a base to give a compound of Formula XI. Examples of the base are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). In this reaction, there can be used a reaction accelerator such as phase-transfer catalysts (e.g. trimethylbenzylammonium chloride) and sodium iodide, and a reaction-inert solvent such as methylene chloride, chloroform, N,N-dimethylformamide, dimethyl sulfoxide, acetone, ethanol, isopropanol, methanol, tetrahydrofuran, acetonitrile and water.

Then, the compound of Formula XI is subjected to sulfonation (e.g. by an ordinary manner using a sulfonating agent in a solvent) and halogenation to give a compound of Formula XII. Examples of the sulfonating agent are sulfuric acid, fuming sulfuric acid, sulfuric anhydride and chlorosulfonic acid. For halogenation, a halogenating agent (e.g. oxalyl chloride, thionyl chloride, phosphorus trichloride, phosphorus pentachloride, phosphoryl chloride and chlorosulfonic acid) is used. Further, a reaction accelerator (e.g. sodium chloride) can be used. Examples of the solvents are reaction-inert solvents such as carbon tetrachloride, methylene chloride, chloroform and 1,1,2,2-tetrachloroethane.

The compound of Formula XII is reduced by an ordinary manner (e.g. using tin, zinc or stannous chloride under acidic conditions) to give a compound of Formula XIII.

The compound of Formula XIII is reacted with the compound of Formula IV in the presence of a base in a solvent to give a compound of Formula IX. Examples of the base are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). Examples of the solvent are reaction-inert solvents such as N,N-dimethylformamide, dimethyl sulfoxide, acetone, ethanol, isopropanol, methanol, tetrahydrofuran, acetonitrile and water.

(3) The compound of Formula I wherein n=O and B is an alkylene group or a group of —CH=CH— can be prepared by a reaction similar to that of the item (1) using a compound represented by the following formula:

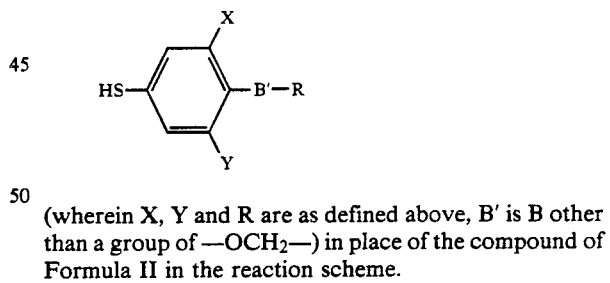

(wherein X, Y and R are as defined above, B' is B other than a group of —OCH$_2$—) in place of the compound of Formula II in the reaction scheme.

(4) In order to prepare the compound of Formula I wherein n is 1, 2 or 3, a compound of the formula:

A—SO$_2$NHCH$_2$CH$_2$S—SCH$_2$CH$_2$NHSO$_2$—A (wherein A is as defined above) is converted into a compound of the formula

A—SO$_2$NHCH$_2$CH$_2$SH (wherein A is as defined above) by an ordinary conversion of a disulfide into a mercaptane (e.g. by reduction using tributylphosphine), and the resulting compound, after isolation or without isolation, is reacted with a compound of the formula

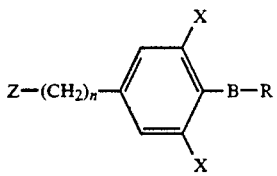

(wherein X, Y, B, R and n are as defined above, and Z is a methylsulfonyloxy group, a chlorine atom, a bromine atom or an iodine atom) in the presence of a base, and further is subjected to hydrolysis of ester as necessary to give the compound of Formula I of the present invention.

Examples of the base used herein are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). Examples of the solvent are reaction-inert solvents such as N,N-dimethylformamide, dimethyl sulfoxide, acetone, ethanol, isopropanol, methanol, tetrahydrofuran, acetonitrile and water.

The compounds of Formula I of the present invention have excellent thromboxane $A_2$ antagonism with low toxicity, and therefore they can be used as blood platelet aggregation inhibiting agents; preventive and therapeutic agents of ischemic disease; preventive and therapeutic agents of cerebrovascular spasm originated after subarachnoid hemorrhage and cerebral ischememia accompanied thereby; and preventive and therapeutic agents of coronary spasm; and therapeutic agents of asthma.

The compound of Formula I' is useful as the preparation intermediate of the compound of Formula I.

For the use of the compound of Formula I for the preventive and therapeutic agents described above, these compounds were mixed with, for example, fillers, binders, disintegrators, pH moderators and solubilizers to obtain a conventional dosage form such as tablets, pills, capsules, granules, powders, solutions, emulsions, suspensions, injectional solutions according to conventional pharmaceutical practices.

The oral or parenteral dosage of the compound of Formula I for adult is from 0.1 to 5000 mg in single or several divided doses per day, but it varies by depending on the kind of diseases, the age, body weight and symptoms of the patient.

Thromboxane $A_2$ antagonism of the compounds of Formula I is illustrated by the following experiments.

Experiment [In Vitro Test in Rabbit]

Citrated blood (one volume of 3.2% sodium citrate: 9 volume of blood) was collected from the carotid artery of male New Zealand strain house rabbits and centrifuged at 150 g at room temperature for 15 minutes to give platelet rich prasma (PRP) as a supernatant. The remaining blood was centrifuged at 1500 g for 10 minutes to give platelet poor prasma (PPP). Platelet count of PRP was adjusted to $50-60 \times 10^4/\mu l$ by dilution of PRP by PPP.

Blood platelet aggregation was determined using (15S)-15-hydroxy-11,9-(epoxymethano)prosta-5(Z),13(E)-dienoic acid (U-46619, made by Sigma Co.) having thromboxane $A_2$ agonism as an aggregation-inducing substance according to the method of Born [Born, G. V. R., Nature, vol. 194, page 927 (1962)].

Namely, a compound of Formula I as a test drug was dissolved in dimethyl sulfoxide and adjusted to the desired concentration with physiological saline solution. 25 μl of the solution was added to 250 μl of PRP and incubated at 37° C. for 3 minutes, and 25 μl of U-46619 (final concentration: 5 μM) was added. The mixture was measured for 5 minutes by means of a blood platelet aggregation ability measurement apparatus (Aggricoda TM.PA-3210, made by Kyoto Daiichi Kagaku Co.) to obtain the maximum aggregation rate, and the concentration of the test drug required to bring 50% inhibition to the maximum aggregation rate ($IC_{50}$) was calculated.

As a comparative drug, 4-[2-(phenylsulfonylamino)ethyl]phenoxyacetic acid (described in U.S. Pat. No. 4,258,058, hereinafter referred to as "BM") was tested as above.

Results are shown in Table 1 wherein the compound numbers are as defined in the following examples.

TABLE 1

| Compound No. | $IC_{50}$ (μM) | Compound No. | $IC_{50}$ (μM) |
|---|---|---|---|
| 52 | 1.1 | 103 | 1.5 |
| 53 | 5.8 | 105 | 4.5 |
| 54 | 2.4 | 106 | 2.0 |
| 55 | 1.7 | 107 | 7.4 |
| 63 | 7.3 | 112 | 0.63 |
| 67 | 1.8 | 113 | 0.30 |
| 68 | 0.3 | 114 | 0.92 |
| 69 | 0.54 | 115 | 0.93 |
| 71 | 1.5 | 119 | 0.58 |
| 74 | 4.5 | 120 | 0.33 |
| 78 | 5.2 | 121 | 0.75 |
| 93 | 1.5 | 125 | 0.67 |
| 94 | 3.1 | BM | 12 |

Experiment 2 [Test of Acute Thrombocytopenia in Mice]

Male ICR mice weighting 25 g were used (7-11 animals for each group).

Thrombocytopenia was induced by injection of an aggregation-inducing substance (U-46619) having thromboxane $A_2$-like action in amount of 25 μg/kg from the caudal vein. At 30 seconds after injection of U-46619, 20 μl of the blood was collected from the femoral artery, and the platelet counts were immediately measured by means of an automatic blood cell counter (CC-180A, made by Toa Iyoudenshi Co.).

The compound of Formula I was suspended in 5% gum arabic solution and administered peritoneally to the test animals 30 seconds prior to injection of U-46619. As a comparative drug, BM was tested as above.

The inhibition ratio of the thrombocytopenia was calculated by the proportion of the decrease ratio of platelet count of the group treated with the test drug to that of the group with 5% gum arabic solution, and the activity was determined by the following criterion.

+: More than 50% inhibition at a dose of 1.0 mg/kg
++: More than 50% inhibition at a dose of 0.3 mg/kg
+++: More than 50% inhibition at a dose of 0.1 mg/kg Results are shown in Table 2 wherein the compound numbers are as defined in the following examples.

TABLE 2

| Compound No. | Activity |
|---|---|
| 67 | + |

TABLE 2-continued

| Compound No. | Activity |
| --- | --- |
| 68 | +++ |
| 69 | ++ |
| 71 | + |
| 93 | + |
| BM | + |

The present invention is illustrated in more detail by the following examples.

EXAMPLE 1

Chlorosulfonic acid (112.6 g) was added dropwise with ice cooling to 2,6-difluorophenol (25 g). The reaction mixture was stirred at room temperature for an hour and poured into ice-water (600 ml), and the separated oily substance was extracted with methylene chloride. The methylene chloride layer was washed successively with water and a saturated aqueous sodium chloride solution, and dried over anhydrous magnesium sulfate. The solvent was evaporated under reduced pressure to give 4-chlorosulfonyl-2,6-difluorophenol (31.5 g).

$^1$-NMR(CDCl$_3$) δ: 6.29(1H, s), 7.50–7.80(2H, m)

To a mixture of 4-chlorosulfonyl-2,6-difluorophenol (31.5 g), tin (87.8 g) and methanol (320 ml) was added dropwise concentrated hydrochloric acid (80 ml) while the reaction temperature was kept at 40° C. The reaction mixture was heated at reflux for 3 hours and poured into ice water (600 ml), and the separated oily substance was extracted with methylene chloride. The methylene chloride layer was washed with a saturated aqueous sodium chloride solution and dried over anhydrous magnesium sulfate. The solvent was evaporated under reduced pressure to give the residue, to which were then added potassium carbonate (24.2 g) and N,N-dimethylformamide (200 ml) under an argon atmosphere. A solution of N-(2-bromoethyl)phthalimide (30.1 g) in N,N-dimethylformamide (100 ml) was added dropwise under ice cooling, and the reaction mixture was stirred at room temperature for 16 hours and poured into 7% hydrochloric acid (1200 ml). The separated oily substance was extracted with ethyl acetate. The ethyl acetate layer was washed with a saturated aqueous sodium chloride solution and dried over anhydrous magnesium sulfate. The solvent was evaporated under reduced pressure to give a residue, which was then crystallized from ethyl acetate - n-hexane to give 4-[2-(phthalimid-2-yl)ethylthio]-2,6-difluorophenol (27.5 g).

m.p. 143°–144.5° C.

To a mixture of 4-[2-(phthalimid-2-yl)ethylthio]-2,6-difluorophenol (15 g), potassium carboante (9.1 g) and N,N-dimethylformamide (50 ml) was added dropwise under ice cooling ethyl bromoacetate (7.4 g). The reaction mixture was stirred at room temperature for 16 hours, and poured into a mixture of concentrated hydrochloric acid (50 ml) and ice (450 g). The separated oily substance was extracted with ethyl acetate, and the ethyl acetate layer was washed with a saturated aqueous sodium chloride solution and dried over anhydrous magnesium sulfate. The solvent was evaporated under reduced pressure to give a residue, which was then crystallized from acetone - n-hexane to give ethyl 4-[2-(phthalimid-2-yl)ethylthio]-2,6-difluorophenoxyacetate (17 g).

m.p. 90.5°–92° C.

To a mixture of ethyl 4-[2-(phthalimid-2-yl)ethylthio]-2,6-difluorophenoxyacetate (6 g), ethanol (50 ml) and methylene chloride (50 ml) was added hydrazine monohydrate (1.4 g), and the reaction mixture was stirred at room temperature for 16 hours. After removal of the resulting insolubles by filtration, the filtrate was washed with water and dried over anhydrous magnesium sulfate and filtered to remove the insolubles. To the filtrate was added triethylamine (1 g), and then 4-chlorophenylsulfonyl chloride (1.8 g) was added dropwise under ice cooling. The reaction mixture was stirred at room temperature for an hour, washed successively with water, an aqueous sodium bicarbonate solution and a saturated aqueous sodium chloride solution and dried over magnesium sulfate. After evaporation of the solvent under reduced pressure, the resulting residue was chromatographed on silica gel column (eluent; methylene chloride:n-hexane=2:1) to give ethyl 4-[2-(phenylsulfonylamino)ethylthio]-2,6-difluorophenoxyacetate (Compound No. 1) (1.5 g).

$^1$H-NMR (CDCl$_3$) δ: 1.28(3H, t, J=6Hz), 2.97(2H, m), 3.14(2H, m), 4.25(2H, q, J=6 Hz), 4.72(2H, s), 4.88(1H, t, J=6 Hz), 6.80(2H, m), 7.46–7.65(3H, m), 7.84(2H, m)

Following the similar manner, there were obtained the following compounds.

Ethyl 4-[2-(4-chlorophenylsulfonylamino)ethylthio]-2,6-difluorophenoxyacetate (Compound No. 2)

$^1$H-NMR (CDCl$_3$) δ: 1.29(3H, t, J=6 Hz), 2.98(2H, m), 3.14(2H, m), 4.25(2H, q, J=6 Hz), 4.73(2H, s), 4.95(1H, t, J=6 Hz), 6.83(2H, m), 7.49(2H, m), 7.78 (2H, m)

Ethyl 4-[2-(4-methylphenylsulfonylamino)ethylthio]-2,6-difluorophenoxyacetate (Compound No. 3)

$^1$H-NMR (CDCl$_3$) δ: 1.29(3H, t, J=6 Hz), 2.43(3H, s), 2.95(2H, m), 3.12(2H, m), 4.25(2H, q, J=6 Hz), 4.72(2H, s), 4.82(1H, t, J=6 Hz), 6.79(2H, m), 7.30(2H, m), 7.72(2H, m)

Methyl 2,6-difluoro-4-[2-(4-fluorophenylsulfonylamino)ethylthio]phenoxyacetate (Compound No. 4)

$^1$H-NMR (CDCl$_3$) δ: 3.0–3.3(4H, m), 3.71(3H, s), 4.84(2H, s), 7.08(2H, m), 7.9–8.1(2H, m), 8.3–8.4(2H, m)

Methyl 2,6-difluoro-4-[2-(4-bromophenylsulfonylamino)ethylthio]phenoxyacetate (Compound No. 5)

$^1$H-NMR (CDCl$_3$) δ: 2.8–3.0(4H, m), 3.76(3H, s), 4.75(2H, s), 5.10(1H, brs), 7.05(2H, m), 7.6–8.1(4H, m)

Methyl 2,6-difluoro-4-[2-(4-nitrophenylsulfonylamino)ethylthio]phenoxyacetate (Compound No. 6)

$^1$H-NMR (CDCl$_3$) δ: 2.8–3.0(4H, m), 3.75(3H, s), 4.76(2H, s), 5.10(1H, brs), 7.08(2H, m), 8.02(2H, d, J=8.8 Hz), 8.40(2H, d, J=8.8 Hz)

Methyl 2,6-difluoro-4-[2-(methylsulfonylamino)ethylthio]phenoxyacetate (Compound No. 7)

$^1$H-NMR (CDCl$_3$) δ: 2.93(3H, s), 2.9–3.3(4H, m), 3.75(3H, s), 4.70(2H, s), 5.10(1H, brs), 6.91(2H, m)

Methyl 2,6-difluoro-4-[2-(octylsulfonylamino)ethylthio]phenoxyacetate (Compound No. 8)

$^1$H-NMR (CDCl$_3$) δ: 0.7–0.9(3H, m), 1.1–1.4(12H, m), 1.6–1.8(2H, m), 2.8–3.3(4H, m), 3.72(3H, s), 4.67(2H, s), 4.82(1H, t, J=5.9 Hz), 6.86(2H, m)

Methyl 2,6-difluoro-4-[2-(4-hexadecylsulfonylamino)ethylthio]phenoxyacetate (Compound No. 9)

¹H-NMR (CDCl₃) δ: 0.8–1.0(3H, m), 1.1–1.4(28H, m), 1.7–1.9(2H, m), 2.9–3.3(4H, m), 3.78(3H, s), 4.73(2H, s), 5.14(1H, t, J=6 Hz), 6.94(2H, m)

Methyl 2,6-difluoro-4-[2-(4-methoxyphenylsulfonylamino)ethylthio]phenoxyacetate (Compound No. 10)

¹H-NMR (CDCl₃) δ: 2.8–3.0(4H, m), 3.69(3H, s), 3.77(3H, s), 4.63(2H, s), 5.07(1H, t, J=6.1 Hz), 6.70(2H, m), 6.86(2H, d, J=8.9 Hz), 7.67(2H, d, J=8.9 Hz)

EXAMPLE 2

Following a procedure similar to that of Example 1 using 2-fluorophenol as a material, there were obtained the following compounds.

Ethyl 4-[2-(phenylsulfonylamino)ethylthio]-2-fluorophenoxyacetate (Compound No. 11)

¹H-NMR (CDCl₃) δ: 1.30(3H, t, J=7 Hz), 2.90(2H, t, J=6 Hz), 3.09(2H, m), 4.27(2H, q, J=7 Hz), 4.67(2H, s), 5.11(1H, t, J=7 Hz), 6.80(1H, t, J=8 Hz), 7.00(2H, m), 7.51(3H, m), 7.82(2H, m)

Ethyl 4-[2-(4-chlorophenylsulfonylamino)ethylthio]-2-fluorophenoxyacetate (Compound No. 12)

¹H-NMR (CDCl₃) δ: 1.30(3H, t, J=6 Hz), 2.91(2H, m), 3.08(2H, m), 4.27(2H, q, J=6 Hz), 4.68(2H, s), 4.90(1H, t, J=6 Hz), 6.80(1H, t, J=8 Hz), 6.99(3H, m), 7.49(2H, m), 7.75(2H, m)

Ethyl 4-[2-(4-methylphenylsulfonylamino)ethylthiol-2-fluorophenoxyacetate (Compound No. 13)

¹H-NMR (CDCl₃) δ: 1.30(3H, t, J=6 Hz), 2.42(3H, s), 2.89(2H, m), 3.07(2H, m), 4.27(2H, q, J=6 Hz), 4.67(2H, s), 4.72(1H, m), 6.80(1H, t, J=8 Hz), 6.95(3H, m), 7.28(2H, m), 7.68(2H, m)

Methyl 2-fluoro-4-[2-(4-fluorophenylsulfonylamino)ethylthio]phenoxyacetate (Compound No. 14)

¹H-NMR (CDCl₃) δ: 2.8–3.2(4H, m), 3.78(3H, s), 4.78(2H, s), 5.2(1H, brs), 7.0–8.1(7H, m)

Methyl 2-fluoro-4-[2-(4-bromophenylsulfonylamino)ethylthio]phenoxyacetate (Compound No. 15)

¹H-NMR (CDCl₃) δ: 2.8–3.2(4H, m), 3.78(3H, s), 4.78(2H, s), 5.2(1H, brs), 7.0–8.0(7H, m)

Methyl 2-fluoro-4-[2-(4-methoxysulfonylamino)ethylthio]phenoxyacetate (Compound No. 16)

¹H-NMR (CDCl₃) δ: 2.8–3.2(4H, m), 3.78(3H, s), 3.84(3H, s), 4.78(2H, s), 5.2(1H, brs), 7.0–7.3(3H, m), 7.5–7.8(4H, m)

Methyl 2-fluoro-4-[2-(4-nitrophenylsulfonylamino)ethylthio]phenoxyacetate (Compound No. 17)

¹H-NMR (CDCl₃) δ: 2.8–3.1(4H, m), 3.78(3H, s), 4.77(2H, s), 5.2(1H, brs), 7.0–7.3(3H, m), 8.0–8.6(4H, m)

Methyl 2-fluoro-4-[2-(methylsulfonylamino)ethylthio]phenoxyacetate (Compound No. 18)

¹H-NMR (CDCl₃) δ:
2.95(3H, s), 2.8–3.2(4H, m), 3.77(3H, s), 4.75(2H, s), 5.1(1H, brs), 6.9–7.4(3H, m)

Methyl 2-fluoro-4-[2-(octylsulfonylamino)ethylthio]phenoxyacetate (Compound No. 19)

¹H-NMR (CDCl₃) δ: 0.8–1.0(3H, m), 1.2–1.8(14H, m), 2.8–3.2(4H, m), 3.78(3H, s), 4.77(2H, s), 5.1(1H, brs), 7.0–7.4(3H, m)

Methyl 2-fluoro-4-[2-(hexadecylsulfonylamino)ethylthio]phenoxyacetate (Compound No. 20)

¹H-NMR (CDCl₃) δ: 0.8–1.0(3H, m), 1.2–1.8(30H, m), 2.8–3.2(4H, m), 3.77(3H, s), 4.75(2H, s), 5.1(1H, brs), 6.9–7.4(3H, m)

EXAMPLE 3

To a mixture of 4-mercaptophenol (3.78 g), potassium carbonate (8.2 g) and N,N-dimethylformamide (40 ml) was added dropwise under ice cooling a solution of N-(2-bromoethyl)phthalimide (7.62 g) in N,N-dimethylformamide (50 ml). The reaction mixture was stirred at room temperature for 16 hours and poured into 3% hydrochloric acid (220 ml), and the resulting crystals were collected by filtration and dried to give N-[2-(4-hydroxyphenylthio)ethyl]phthalimide (9.1 g).

m.p. 124°–125° C.

To a mixture of N-[2-(4-hydroxyphenylthio)ethyl]phthalimide (7.8 g) obtained above, potassium carbonate (7.2 g) and N,N-dimethylformamide (50 ml) was added dropwise under ice cooling ethyl bromoacetate (2.9 ml). The reaction mixture was warmed to 60° C., stirred for 3 hours, poured into 3% hydrochloric acid (220 ml) and extracted with ethyl acetate. The ethyl acetate layer was washed twice with a saturated aqueous sodium chloride solution and dried over anhydrous magnesium sulfate. Evaporation of the solvent under reduced pressure gave a residue, which was then recrystallized from n-hexane to give ethyl 4-[2-(phthalimid-2-yl)ethylthio]-phenoxyacetate (10.0 g).

m.p. 91°–92° C.

A mixture of ethyl 4-[2-(phthalimid-2-yl)ethylthio]-phenoxyacetate (9.9 g), methylene chloride (100 ml), ethanol (100 ml) and hydrazine monohydrate (2.5 ml) was stirred at room temperature for 16 hours. After removal of the resulting insolubles by filtration, the filtrate was washed with water and dried over anhydrous magnesium sulfate, and the insolubles were removed by filtration.

To the filtrate obtained above was added triethylamine (3.8 ml) and then benzenesulfonyl chloride (4.54 g) was added dropwise under ice cooling. The reaction mixture was stirred at room temperature for 30 minutes, washed successively with water, an aqueous sodium bicarbonate solution and a saturated aqueous sodium chloride solution and dried over anhydrous magnesium sulfate. Evaporation of the solvent under reduced pressure gave a residue, which was then chromatographed on silica gel column (eluent; ethyl acetate:n-hexane=2:3) to give ethyl 4-[2-(phenylsulfonylamino)ethylthio]phenoxyacetate (Compound No. 21) (5.9 g).

¹H-NMR (CDCl₃) δ: 1.29(3H, t, J=7 Hz), 2.83(2H, t, J=6 Hz), 3.04(2H, brq), 4.27(2H, q, J=7 Hz), 4.60(2H, s), 5.10(1H, brs), 6.76(2H, m), 7.20(2H, m), 7.51(3H, m), 7.80(2H, m)

Following a similar manner to that of Example 3, there were obtained the following compounds.

Ethyl 4-[2-(4-chlorophenylsulfonylamino)ethylthio]-phenoxyacetate (Compound No. 22)

¹H-NMR (CDCl₃) δ: 1.30(3H, t, J=7 Hz), 2.86(2H, t, J=6 Hz), 3.04(2H, q, J=6 Hz), 4.28(2H, q, J=7 Hz), 4.60(2H, s), 4.90(1H, brt), 6.78(2H, m), 7.18(2H, m), 7.46(2H, m), 7.73(2H, m)

Methyl 4-[2-(4-methylphenylsulfonylamino)ethylthio]phenoxyacetate (Compound No. 23)

¹H-NMR (CDCl₃) δ: 2.37(3H, s), 2.8–3.2(4H, m), 3.76(3H, s), 4.66(2H, s), 5.2(1H, brs), 6.9–7.7(8H, m)

Methyl 4-[2-(4-methoxyphenylsulfonylamino)ethylthio]phenoxyacetate (Compound No. 24)

¹H-NMR (CDCl₃) δ: 2.8–3.2(4H, m), 3.76(3H, s), 3.83(3H, s), 4.65(2H, s), 5.2(1H, brs) 6.9–7.2(4H, m), 7.3–7.7(4H, m)

Methyl 4-[2-(4-fluorophenylsulfonylamino)ethylthio]phenoxyacetate (Compound No. 25)

$^1$H-NMR (CDCl$_3$) δ: 2.8–3.1(4H, m), 3.78(3H, s), 4.66(2H, s), 5.2(1H, brs), 6.9–7.3(4H, m), 7.5–8.0(4H, m)

Methyl 4-[2-(4-bromophenylsulfonylamino)ethylthio]phenoxyacetate (Compound No. 26)

$^1$H-NMR (CDCl$_3$) δ: 2.8–3.2(4H, m), 3.78(3H, s), 4.68(2H, s), 5.2(1H, brs), 6.9–7.4(4H, m), 7.7–8.1(4H, m)

Methyl 4-[2-(2,5-dichlorophenylsulfonylamino)ethylthio]phenoxyacetate (Compound No. 27)

$^1$H-NMR (CDCl$_3$) δ: 2.8–3.2(4H, m), 3.77(3H, s), 4.67(2H, s), 5.2(1H, brs), 6.9–7.3(4H, m), 7.8–8.0(3H, m)

Methyl 4-[2-(2,4,5-trichlorophenylsulfonylamino)ethylthio]phenoxyacetate (Compound No. 28)

$^1$H-NMR (CDCl$_3$) δ: 2.8–3.2(4H, m), 3.76(3H, s), 4.66(2H, s), 6.9–7.2(4H, m), 5.1(1H, brs), 8.0–8.1(2H, m)

Methyl 4-[2-(2,3,4,5,6-pentafluorophenylsulfonylamino)ethylthio]phenoxyacetate (Compound No. 29)

$^1$H-NMR (CDCl$_3$) δ: 2.9–3.3(4H, m), 3.78(3H, s), 4.67(2H, s), 5.1(1H, brs), 6.9–7.3(4H, m)

Methyl 4-[2-(2,4,6-trimethylphenylsulfonylamino)ethylthio]phenoxyacetate (Compound No. 30)

$^1$H-NMR (CDCl$_3$) δ: 2.26(3H, s), 2.49(6H, s), 2.8–3.2(4H, m), 3.78(3H, s), 4.66(2H, s), 5.2(1H, brs), 6.9–7.2(6H, m)

Methyl 4-[2-(2,4,6-triisopropylphenylsulfonylamino)ethylthio]phenoxyacetate (Compound No. 31)

$^1$H-NMR (CDCl$_3$) δ: 1.2–1.3(18H, m), 2.8–3.2(7H, m), 3.77(3H, s), 4.65(2H, s), 5.2(1H, brs), 6.8–7.2(6H, m)

Methyl 4-[2-(2-naphthylsulfonylamino)ethylthio]phenoxyacetate (Compound No. 32)

$^1$H-NMR (CDCl$_3$) δ: 2.8–3.2(4H, m), 3.78(3H, s), 4.65(2H, s), 5.2(1H, brs), 6.8–7.1(4H, m), 7.7–8.4(7H, m)

Methyl 4-[2-(4-nitrophenylsulfonylamino)ethylthio]phenoxyacetate (Compound No. 33)

$^1$H-NMR (CDCl$_3$) δ: 2.8–3.2(4H, m), 3.78(3H, s), 4.66(2H, s), 5.1(1H, brs), 6.9–7.2(4H, m), 8.0–8.4(4H, m)

Methyl 4-[2-(4-chloro-3-nitrophenylsulfonylamino)ethylthio]phenoxyacetate (Compound No. 34)

$^1$H-NMR (CDCl$_3$) δ: 2.8–3.2(4H, m), 3.76(3H, s), 4.66(2H, s), 5.2(1H, brs), 6.9–7.2(4H, m), 8.0–8.4(4H, m)

Methyl 4-[2-(4-acetylaminophenylsulfonylamino)ethylthio]phenoxyacetate (Compound No. 35)

$^1$H-NMR (CDCl$_3$) δ: 2.08(3H, s), 2.5–2.9(4H, m), 3.52(3H, s), 4.11(2H, s), 5.2(1H, brs), 6.7–7.5(8H, m)

Methyl 4-[2-(3-pyridylsulfonylamino)ethylthio]phenoxyacetate (Compound No. 36)

$^1$H-NMR (CDCl$_3$) δ: 2.8–3.2(4H, m), 3.77(3H, s), 4.68(2H, s), 5.1(1H, brs), 6.9–7.3(4H, m), 7.5–8.9(4H, m)

Methyl 4-[2-(3,5-dichloro-2-hydroxyphenylsulfonylamino)ethylthio]phenoxyacetate (Compound No. 37)

$^1$H-NMR (CDCl$_3$) δ: 2.8–3.1(4H, m), 3.76(3H, s), 4.65(2H, s), 5.2(1H, brs), 6.8–7.2(4H, m), 7.6–7.8(2H, m)

EXAMPLE 4

To a solution of ethyl 4-[2-(phenylsulfonylamino)ethylthio]phenoxyacetate (2 g) obtained in Example 3 in methylene chloride (30 ml) was added dropwise under ice cooling a solution of m-chloroperbenzoic acid (0.87 g) in methylene chloride (20 ml). The reaction mixture was stirred at room temperature for an hour, washed with an aqueous sodium bicarbonate solution and dried over anhydrous magnesium sulfate. Evaporation of the solvent under reduced pressure gave a residue, which was then chromatographed on silica gel column (eluent; ethyl acetate) and recrystallized from ethyl acetate to give ethyl 4-[2-(phenylsulfonylamino)ethylsulfinyl]phenoxyacetate (Compound No. 38) (1.76 g).

m.p. 116°–118.5° C.

Following a similar manner to that of Example 4, there was obtained ethyl 4-[2-(4-chlorophenylsulfonylamino)ethylsulfinyl]-2,6-difluorophenoxyacetate (Compound No. 39).

m.p. 137°–138° C.

EXAMPLE 5

To a solution of ethyl 4-[2-(phenylsulfonylamino)ethylthio]phenoxyacetate (1.8 g) obtained in Example 3 in methylene chloride (30 ml) was added dropwise under ice cooling a solution of m-chloroperbenzoic acid (1.57 g) in methylene chloride (40 ml). The reaction mixture was stirred at room temperature for an hour, washed with an aqueous sodium bicarbonate solution and dried over anhydrous magnesium sulfate. Evaporation of the solvent under reduced pressure gave a residue, which was chromatographed on silica gel column (eluent; ethyl acetate) to give ethyl 4-[2-(phenylsulfonylamino)ethylsulfonyl]phenoxyacetate (Compound No. 40) (1.94 g).

m.p. 86.5°–88° C.

Following a similar manner to that of Example 5, there was obtained ethyl 4-[2-(4-chlorophenylsulfonylamino)ethylsulfonyl]-2,6-difluorophenoxyacetate (Compound No. 41).

m.p. 166°–167° C.

EXAMPLE 6

Chlorosulfonic acid (87 ml) was added dropwise to ethyl phenylacetate (48 g), and the mixture was stirred at 40° C. for 30 minutes. The reaction mixture was poured into ice water (1000 ml), and the separated oily substance was extracted with methylene chloride. The methylene chloride layer was washed successively with water and a saturated aqueous sodium chloride solution and dried over anhydrous magnesium sulfate. Evaporation of the solvent under reduced pressure gave ethyl 4-chlorosulfonylphenylacetate (42 g).

$^1$H-NMR (CDCl$_3$) δ: 1.25(3H, t, J=7 Hz), 3.11(2H, s), 4.20(2H, q, J=7 Hz), 7.55(2H, m), 8.00(2H, m)

To a mixture of ethyl 4-chlorosulfonylphenylacetate (42 g) obtained above, tin (96 g) and methanol (320 ml) was added dropwise at 40° C. conc. hydrochloric acid (80 ml). The reaction mixture was heated at reflux for 3 hours and poured into ice water (600 ml), and the separated oily substance was extracted with methylene chloride. The methylene chloride layer was washed successively with water and a saturated aqueous sodium chloride solution and dried over anhydrous magnesium sulfate, and the solvent was evaporated under reduced pressure. To the resulting residue were added under an argon atmosphere potassium carbonate (16.4 g) and N,N-dimethylformamide (100 ml). Then, a solution of N-(2-bromoethyl)phthalimide (20.3 g) in N,N-dimethylformamide (100 ml) was added dropwise under ice cooling. The reaction mixture was stirred at room temperature for 16 hours and poured into 7% hydrochloric acid (1200 ml), and the separated oily substance was extracted with ethyl acetate. The ethyl acetate layer was washed with a saturated aqueous sodium chloride solution and dried over anhydrous magnesium sulfate. Evaporation of the solvent under reduced pressure gave a residue, which was chromatographed on silica gel column (eluent; methylene chloride:n-hexane=1:1) and crystallized from methylene chloride - n-hexane to give methyl 4-[2-(phthalimid-2-yl)ethylthio]phenylacetate (9.1 g).

m.p. 90°–92° C.

Following a similar manner to that of Example 1 using methyl 4-[2-(phthalimid-2-yl)ethylthio]phenylacetate, there was obtained methyl 4-[2-(phenylsulfonylamino)ethylthio]phenylacetate (Compound No. 42).

$^1$H-NMR (CDCl$_3$) δ: 2.95(2H, t, J=7 Hz), 3.12(2H, m), 3.57(2H, s), 3.70(3H, s), 4.95(1H, brm), 7.16(3H, m), 7.50(2H, m), 7.82(2H, m)

In a similar manner, there were obtained the following compounds.

Methyl 4-[2-(4-chlorophenylsulfonylamino)ethylthio]phenylacetate (Compound No. 43)

$^1$H-NMR (CDCl$_3$) δ: 2.98(2H, m), 3.11(2H, m), 3.60(2H, s), 3.70(3H, s), 7.18(4H, m), 7.44(2H, m), 7.74(2H, m)

Methyl 4-[2-(4-methylphenylsulfonylamino)ethylthio]phenylacetate (Compound No. 44)

$^1$H-NMR (CDCl$_3$) δ: 2.43(3H, s), 2.95(2H, m), 3.10(2H, m), 3.58(2H, s), 3.70(3H, s), 4.93(1H, t, J=6 Hz), 7.18(4H, m), 7.28(2H, m), 7.71(2H, m)

Methyl 4-[2-(4-fluorophenylsulfonylamino)ethylthio]phenylacetate (Compound No. 45)

$^1$H-NMR (CDCl$_3$) δ: 2.9–3.3(4H, m), 3.55(2H, s), 3.78(3H, s), 5.1(1H, brs), 7.1–8.1(8H, m)

Methyl 4-[2-(4-bromophenylsulfonylamino)ethylthio]phenylacetate (Compound No. 46)

$^1$H-NMR (CDCl$_3$) δ: 2.9–3.2(4H, m), 3.56(2H, s), 3.77(3H, s), 5.2(1H, brs), 7.1–8.1(8H, m)

Methyl 4-[2-(4-methoxyphenylsulfonylamino)ethylthio]phenylacetate (Compound No. 47)

$^1$H-NMR (CDCl$_3$) δ:
2.9–3.2(4H, m), 3.55(2H, s), 3.78(3H, s), 3.82(3H, s), 5.2(1H, brs), 7.1–7.4(4H, m), 7.6–8.0(4H, m)

Methyl 4-[2-(4-nitrophenylsulfonylamino)ethylthio]phenylacetate (Compound No. 48)

$^1$H-NMR (CDCl$_3$) δ: 2.9–3.4(4H, m), 3.56(2H, s), 3.75(3H, s), 7.0–7.3(4H, m), 5.2(1H, brs), 8.0–8.5(4H, m)

Methyl 4-[2-(methylsulfonylamino)ethylthio]phenylacetate (Compound No. 49)

$^1$H-NMR (CDCl$_3$) δ: 2.90(3H, s), 2.9–3.3(4H, m), 3.55(2H, s), 3.76(3H, s), 5.2(1H, brs), 7.1–7.4(4H, m)

Methyl 4-[2-(octylsulfonylamino)ethylthio]phenylacetate (Compound No. 50)

$^1$H-NMR (CDCl$_3$) δ: 0.7–0.9(3H, m), 1.2–1.8(14H, m), 2.9–3.4(4H, m), 3.55(2H, s), 3.76(3H, s), 5.1(1H, brs), 7.1–7.4(4H, m)

Methyl 4-[2-(hexadecylsulfonylamino)ethylthio]phenylacetate (Compound No. 51)

$^1$H-NMR (CDCl$_3$) δ: 0.7–0.9(3H, m), 1.2–1.8(30H, m), 2.9–3.4(4H, m), 3.56(2H, s), 3.78(3H, s), 5.2(1H, brs), 7.1–7.4(4H, m)

EXAMPLE 7

To a mixture of 3-(4-mercaptophenyl)propionic acid (1.82 g), potassium carbonate (5.6 g) and N,N-dimethylformamide (12 ml) was added N-(2-bromoethyl)phthalimide (2.54 g), and the mixture was stirred at room temperature for 3.5 hours. The reaction mixture was poured into 2% hydrochloric acid (150 ml), and extracted with ethyl acetate. The ethyl acetate layer was washed twice with a saturated aqueous sodium chloride solution and dried over anhydrous magnesium sulfate. Evaporation of the solvent under reduced pressure gave 3-{4-[2-(phthalimid-2-yl)ethylthio]phenyl}propionic acid (3.58 g).

m.p. 105.5°–107° C.

A mixture of 3-{4-[2-(phenylimid-2-yl)ethylthio]phenyl}propionic acid (3.4 g), hydrazine monohydrate (3.85 ml) and methanol (30 ml) was heated at reflux with stirring for an hour. After cooling the reaction mixture, the resulting insolubles were removed by filtration, and the filtrate was evaporated under reduced pressure. The residue was chromatographed (Diaion HP-20, eluent; water - methanol) to give 3-[4-(2-aminoethylthio)phenyl]propionic acid (1.75 g).

m.p. 90°–110° C.

To a mixture of 3-[4-(2-aminoethylthio)phenyl]propionic acid (0.8 g), triethylamine (1.6 ml) and methylene chloride (50 ml) was added 4-chlorophenylsulfonyl chloride (0.79 g), and the mixture was stirred at room temperature for 16 hours. The reaction mixture was washed successively with 3% hydrochloric acid and a saturated aqueous sodium chloride solution, and dried over anhydrous magnesium sulfate. Evaporation of the solvent under reduced pressure gave a residue, which was then crystallized from ethyl acetate - n-hexane to give 3-{4-[2-(4-chlorophenylsulfonylamino)ethylthio]phenyl}propionic acid (Compound No. 52) (1.07 g).

m.p. 117°–119° C.

Following a similar manner to that of Example 7, there were obtained the following compounds.

3-{4-[2-(4-Methylphenylsulfonylamino)ethylthio]phenyl}propionic acid (Compound No. 53)

m.p. 127.3°–130.4° C.

3-{4-[2-(4-Fluorophenylsulfonylamino)ethylthio]phenyl}propionic acid (Compound No. 54)

m.p. 135°–136.5° C.

3-{4-[2-(4-Bromophenylsulfonylamino)ethylthio]phenyl}propionic acid (Compound No. 55)

m.p. 129.7°–133.5° C.

3-{4-[2-(2,3,4,5,6-Pentafluorophenylsulfonylamino)ethylthio]phenyl}propionic acid (Compound No. 56)

m.p. 131.5°–133.6° C.

Potassium 3-{4-[2-(2,4,6-trimethylphenylsulfonylamino)ethylthio]phenyl}propionate (Compound No. 57)

$^1$H-NMR (DMSO-d$_6$) δ: 1.65(1H, s), 2.1–2.2(2H, m), 2.25(3H, s), 2.51(6H, s), 2.7–2.9(6H, m), 6.99(2H, s), 7.08(4H, s)

3-{4-[2-(3,4-Dichloro-6-hydroxyphenylsulfonylamino)ethylthio]phenyl}propionic acid (Compound No. 58)

m.p. 139°–141.4° C.

3-{4-[2-(3-Nitro-4-chlorophenylsulfonylamino)ethylthio]phenyl}propionic acid (Compound No. 59)

m.p. 125.1°–127.7° C.

3-{4-[2-(4-acetamidophenylsulfonylamino)ethylthio]phenyl}propionic acid (Compound No. 60)

m.p. 146.5°–148.9° C.

3-{4-[2-(3-Pyridylsulfonylamino)ethylthio]propionic acid (Compound No. 61)

m.p. 146.7°–149.8° C.

EXAMPLE 8

A mixture of bis[2-(phenylsulfonylamino)ethyl]disulfide (1 g), tributylphosphine (0.72 ml) and 90% methanol (30 ml) was stirred under an argon atmosphere at room temperature for 30 minutes, and the reaction mixture was evaporated under reduced pressure. To the residue were added under an argon atmosphere triethylamine (1.4 ml) and ethanol (10 ml). Then, ethyl 4- chloromethylphenoxyacetate (1.05 g) was added, and the mixture was stirred at room temperature for 16 hours. The reaction mixture was evaporated under reduced pressure, and the resulting residue was chromatographed on silica gel column (eluent:ethyl acetate - n-hexane=1:3) to give ethyl 4-[2-(phenylsulfonylamino)ethylthiomethyl]phenoxyacetate (Compound No. 62) (1.04 g).

$^1$-NMR (CDCl$_3$) δ: 1.30(3H, t, J=7 Hz), 2.49(2H, t, J=6 Hz), 3.02(2H, brs), 3.51(2H, s), 4.25(2H, q, J=7 Hz), 4.59(2H, s), 4.98(1H, brs), 6.80(2H, m), 7.13(2H, m), 7.55(3H, m), 7.83(2H, m)

In a similar manner, there was obtained the following Compound.

Ethyl 4-[2-(4-chlorophenylsulfonylamino)ethylthiomethyl]phenoxyacetate (Compound No. 63)
m.p. 52.5°–53.5° C.

EXAMPLE 9

To a solution of methyl 4-formylcinnamate (5.58 g) in methanol (100 ml) was added sodium borohydride (0.4 g), and the mixture was stirred at room temperature for an hour. The reaction mixture was poured into water and extracted with methylene chloride. The methylene chloride layer was washed with a saturated aqueous sodium chloride solution and dried over anhydrous magnesium sulfate. Evaporation of the solvent under reduced pressure gave methyl 4-(hydroxymethyl)cinnamate (5.27 g).
m.p. 86°–87° C.

To a mixture of methyl 4-(hydroxymethyl)cinnamate (4.1 g), triethylamine (3.1 ml) and methylene chloride (50 ml) was added dropwise under ice cooling methanesulfonyl chloride (1.7 ml), and the mixture was stirred at room temperature for 1.5 hours. Evaporation of the reaction solution gave a residue, which was then chromatographed on silica gel column (eluent: methylene chloride) to give methyl 4-(chloromethyl)cinnamate (2.57 g).

$^1$H-NMR (CDCl$_3$) δ: 3.80(3H, s), 4.60(2H, s), 6.44(1H, d, J=15 Hz), 7.40(2H, m), 7.51(2H, m), 7.69(1H, d, J=15 Hz)

A mixture of bis[2-(4-chlorophenylsulfonylamino)ethyl]disulfide (1.2 g), tributylphosphine (0.65 ml) and 90% methanol (30 ml) was stirred under an argon atmosphere at room temperature for 30 minutes, and the reaction mixture was evaporated under reduced pressure. To the residue were added under an argon atmosphere potassium carbonate (1.3 g) and N,N-dimethylformamide (20 ml). Then, methyl 4-chloromethylcinnamate (1 g) obtained above was added thereto, and the mixture was stirred at room temperature for 16 hours. To the reaction mixture was added ethyl acetate, and the mixture was washed twice with a saturated aqueous sodium chloride solution and dried over anhydrous magnesium sulfate. Evaporation of the solvent under reduced pressure gave methyl 4-[2-(4-chlorophenylsulfonylamino)ethylthiomethyl]cinnamate (Compound No. 64) (1.74 g).
m.p. 99°–103° C.

EXAMPLE 10

Following a similar manner to that of Example 9 using ethyl 4-[2-(methylsulfonyloxy)ethyl]phenoxyacetate or ethyl 4-[3-(methylsulfonyloxy)propyl]phenoxyacetate, there were obtained the following compounds.

Ethyl 4-{2-[2-(phenylsulfonylamino)ethylthio]ethyl}phenoxyacetate (Compound No. 65)

$^1$H-NMR (CDCl$_3$) δ: 1.30(3H, t, J=7 Hz), 2.53(2H, t, J=6 Hz), 2.58(2H, m), 2.72(2H, m), 3.10(2H, brq, J=6 Hz), 4.26(2H, q, J=7 Hz), 4.60(2H, s), 5.00(1H, brs), 6.83(2H, m), 7.05(2H, m), 7.50(3H, m), 7.85(2H, m)

Ethyl 4-{2-[3-(phenylsulfonylamino)propylthio]ethyl}phenoxyacetate (Compound No. 66)

$^1$H-NMR (CDCl$_3$) δ: 1.30(3H, t, J=7 Hz), 1.76(2H, m), 2.35(2H, t, J=6 Hz), 2.59(4H, m), 3.10(2H, brs), 4.25(2H, q, J=7 Hz), 4.60(2H, s), 4.98(1H, brs), 6.82(2H, m), 7.02(2H, m), 7.52(3H, m), 7.85(2H, m)

EXAMPLE 11

To a mixture of ethyl 2,6-difluoro-4-[2-(phenylsulfonylamino)ethylthio]phenoxyacetate (1.5 g) and ethanol (12 ml) was added 10% sodium hydroxide (3 ml), and the mixture was stirred at room temperature for 30 minutes. The reaction mixture was made acidic with 3% hydrochloric acid and extracted with ethyl acetate. The ethyl acetate layer was washed with a saturated aqueous sodium chloride solution and dried over anhydrous magnesium sulfate. Evaporation of the solvent under reduced pressure gave 2,6-difluoro-4-[2-(phenylsulfonylamino)ethylthio]phenoxyacetic acid (Compound No. 67) (1.3 g).
m.p. 91°–93° C.

In a similar manner, there were obtained the following compounds from the compounds obtained in Examples 1–6, and 8–10.

2.6-Difluoro-4-[2-(4-chlorophenylsulfonylamino)ethylthio]phenoxyacetic acid (Compound No. 68)
m.p 97°–98° C.

2,6-Difluoro-4-[2-(4-methylphenylsulfonylamino)ethylthio]phenoxyacetic acid (Compound No. 69)
m.p. 93°–95° C.

2-Fluoro-4-[2-(phenylsulfonylamino)ethylthio]phenoxyacetic acid (Compound No. 70)
m.p. 122°–126° C.

2-Fluoro-4-[2-(4-chlorophenylsulfonylamino)ethylthio]phenoxyacetic acid (Compound No. 71)
m.p. 111°–113.5° C.

2-Fluoro-4-[2-(4-methylphenylsulfonylamino)ethylthio]phenoxyacetic acid (Compound No. 72)
m.p. 120.5°–122.5° C.

4-[2-(Phenylsulfonylamino)ethylthio]phenoxyacetic acid (Compound No. 73)
m.p. 156°–159° C.

4-[2-(4-Chlorophenylsulfonylamino)ethylthio]phenoxyacetic acid (Compound No. 74)
m.p 142.5°–144° C.

4-[2-(4-Methylphenylsulfonylamino)ethylthio]phenoxyacetic acid (Compound No. 75)
m.p. 152.8°–155.1° C.

4-[2-(4-Methoxyphenylsulfonylamino)ethylthio]phenoxyacetic acid (Compound No. 76)
m.p. 128.7°–130.9° C.

4-[2-(4-Fluorophenylsulfonylamino)ethylthio]phenoxyacetic acid (Compound No. 77)
m.p. 150.5°–153.5° C.

4-[2-(4-Bromophenylsulfonylamino)ethylthio]phenoxyacetic acid (Compound No. 78)
m.p. 151.9°–153.4° C.

4-[2-(2,5-Dichlorophenylsulfonylamino)ethylthio]phenoxyacetic acid (Compound No. 79)
m.p. 143.5°–145.9° C.

4-[2-(2,4,5-Trichlorophenylsulfonylamino)ethylthio]phenoxyacetic acid (Compound No. 80)

m.p. 125.4°–127.2° C.

4-[2-(2,3,4,5,6-Pentafluorophenylsulfonylamino)ethylthio]phenoxyacetic acid (Compound No. 81)
m.p. 113.5°–116.3° C.

4-[2-(2,4,6-Trimethylphenylsulfonylamino)ethylthio]phenoxyacetic acid (Compound No. 82)
m.p. 129.4°–131.4° C.

4-[2-(2,4,6-Triisopropylphenylsulfonylamino)ethylthio]phenoxyacetic acid (Compound No. 83)
m.p. 180.5°–183.5° C.

4-[2-(2-Naphthylsulfonylamino)ethylthio]phenoxyacetic acid (Compound No. 84)
m.p 74°–79.5° C.

4-[2-(4-Nitrophenylsulfonylamino)ethylthio]phenoxyacetic acid (Compound No. 85)
m.p. 160.4°–162.5° C.

4-[2-(4-Chloro-3-nitrophenylsulfonylamino)ethylthio]phenoxyacetic acid (Compound No. 86)
m.p. 91.5°–95.8° C.

Potassium 4-[2-(4-acetylaminophenylsulfonylamino)ethylthio]phenoxyacetate (Compound No. 87)
$^1$H-NMR (DMSO-d$_6$) δ: 2.07(3H, s), 2.5–2.8(4H, m), 4.11(2H, s), 6.69(2H, d, J=9 Hz), 7.09(2H, d, J=9 Hz), 7.3–7.6(4H, m)

4-[2-(3-Pyridylsulfonylamino)ethylthio]phenoxyacetic acid (Compound No. 88)
m.p. 163.2°–165.1° C.

4-[2-(3,5-Dichloro-4-hydroxyphenylsulfonylamino)ethylthio]phenoxyacetic acid (Compound No. 89)
m.p. 125.3°–129.4° C.

4-[2-(Phenylsulfonylamino)ethylsulfinyl]phenoxyacetic acid (Compound No. 90)
m.p. 182.5°–183.5° C.

4-[2-(Phenylsulfonylamino)ethylsulfonyl]phenoxyacetic acid (Compound No. 91)
m.p. 156°–158.5° C.

Sodium 4-[2-(phenylsulfonylamino)ethylthio]phenylacetate (Compound No. 92)
m.p 157.5°–159.5° C.

4-[2-(4-Chlorophenylsulfonylamino)ethylthio]phenylacetic acid (Compound No. 93)
m.p. 129°–131° C.

4-[2-(4-Methylsulfonylamino)ethylthio]phenylacetic acid (Compound No. 94)
m.p. 95°–97° C.

Sodium 4-[2-(phenylsulfonylamino)ethylthiomethyl]phenylacetate (Compound No. 95)
$^1$H-NMR (DMSO-d$_6$) δ: 2.38(2H, m), 2.80(2H, m), 3.50(2H, s), 4.09(2H, s), 6.70(2H, m), 7.05(2H, m), 7.33(3H, m), 7.60(2H, m)

4-[2-(4-Chlorophenylsulfonylamino)ethylthiomethyl]phenoxyacetic acid (Compound No. 96)
m.p. 123°–124° C.

4-[2-(4-Chlorophenylsulfonylamino)ethylthiomethyl]cinnamic acid (Compound No. 97)
m.p. 173°–174° C.

Sodium 4-{2-[(2-phenylsulfonylamino)ethylthioethyl]phenoxyacetate (Compound No. 98)
$^1$H-NMR (DMSO$_6$) δ: 2.40(2H, dd, J=6, 8 Hz), 2.60(4H, m), 2.80(2H, dd, J=6, 8 Hz), 4.08(2H, s), 6.70(2H, m), 7.00(2H, m), 7.85(3H, m), 7.62(2H, m)

Sodium 4-{2-[(2-phenylsulfonylamino)propylthioethyl}phenoxyacetate (Compound No. 99)
$^1$H-NMR (DMSO-d$_6$) δ: 1.65(2H, m), 2.35(4H, m), 2.75(2H, m), 4.06(2H, s), 6.70(2H, m), 7.00(2H, m), 7.33(3H, m), 7.60(2H, m)

3-{4-[2-(Phenylsulfonylamino)ethylthio]phenyl}propionic acid (Compound No. 100)
m.p. 146.2°–148.1° C.

3-{4-[2-(2-naphthylsulfonylamino)ethylthio]phenyl} propionic acid (Compound No. 101)
m.p. 132.1°–134.5° C.

3-{4-[2-(2,4,6-Triisopropylphenylsulfonylamino)ethylthio]phenyl}propionic acid (Compound No. 102)
m.p. 113.5°–116.9° C.

3-{4-[2-(4-Nitrophenylsulfonylamino)ethylthio]phenyl}propionic acid (Compound No. 103)
m.p. 154°–156.2° C.

3-{-4-[2-(2,4,5-Trichlorophenylsulfonylamino)ethylthio]phenyl}propionic acid (Compound No. 104)
m.p. 123.4°–126.6° C.

2-Fluoro-4-[2-(4-fluorophenylsulfonylamino)ethylthio]phenoxyacetic acid (Compound No. 105)
m.p. 126°–128° C.

2-Fluoro-4-[2-(4-bromophenylsulfonylamino)ethylthio]phenoxyacetic acid (Compound No. 106)
m.p 118.2°–120.4° C.

2-Fluoro-4-[2-(4-methoxyphenylsulfonylamino)ethylthio]phenoxyacetic acid (Compound No. 107)
m.p. 144°–146.1° C.

2-Fluoro-4-[2-(4-nitrophenylsuflonylamino)ethylthio]phenoxyacetic acid (Compound No. 108)
m.p. 140°–142° C.

2-Fluoro-4-[2-(methylsulfonylamino)ethylthio]phenoxyacetic acid (Compound No. 109)
m.p. 88.8°–91.3° C.

2-Fluoro-4-[2-(octylsulfonylamino)ethylthio]phenoxyacetic acid (Compound No. 110)
m.p. 107.6°–109.3° C.

2-Fluoro-4-[2-(hexadecylsulfonylamino)ethylthio]phenoxyacetic acid (Compound No. 111)
m.p. 120.4°–123.3° C.

4-[2-(4-Fluorophenylsulfonylamino)ethylthio]phenylacetic acid (Compound No. 112)
m.p 102.8°–105.6° C.

4-[2-(4-Bromophenylsulfonylamino)ethylthio]phenylacetic acid (Compound No. 113)
m.p. 126°–129.6° C.

4-[2-(4-Methoxyphenylsulfonylamino)ethylthio]phenylacetic acid (Compound No. 114)
m.p. 84.5°–87.4° C.

4-[2-(4-Nitrophenylsulfonylamino)ethylthio]phenylacetic acid (Compound No. 115)
m.p. 114.6°–117.9° C.

4-[2-(Methylsulfonylamino)ethylthio]phenylacetic acid (Compound No. 116)
m.p. 108.3°–111° C.

4-[2-(Octylsulfonylamino)ethylthio]phenylacetic acid (Compound No. 117)
m.p. 111.9°–114.6° C.

4-[2-(Hexadecylsulfonylamino)ethylthio]phenylacetic acid (Compound No. 118)
m.p. 111.8°–114.3° C.

2,6-Difluoro-4-[2-(4-fluorophenylsulfonylamino)ethylthio]phenoxyacetic acid (Compound No. 119)
m.p. 84.8°–87.7° C.

2,6-Difluoro-4-[2-(4-bromophenylsulfonylamino)ethylthio]phenoxyacetic acid (Compound No. 120)
m.p. 113.4°–116.5° C.

2,6-Difluoro-4-[2-(4-nitrophenylsulfonylamino)ethylthio]phenoxyacetic acid (Compound No. 121)
m.p. 115.6°–119° C.

2,6-Difluoro-4-[2-(methylsulfonylamino)ethylthio]phenoxyacetic acid (Compound No. 122)

m.p 117.8°–121.5° C.

2,6-Difluoro-4-[2-(octylsulfonylamino)ethylthio]-phenoxyacetic acid (Compound No. 123)
m.p. 98°–101.3° C.

2,6-Difluoro-4-[2-(4-hexadecylsulfonylamino)ethyl-thio]phenoxyacetic acid (Compound No. 124)
m.p. 118.8°–120.9° C.

2,6-Difluoro-4-[2-(4-methoxyphenylsulfonylamino)e-thylthio]phenoxyacetic acid (Compound No. 125)
$^1$H-NMR (CDCl$_3$) δ: 2.9–3.2(4H, m), 3.87(3H, s), 4.78(2H, s), 5.2(1H, brs), 6.7–7.0(4H, m), 7.6–7.8(2H, m), 8.5(1H, brs)

4-[2-(4-Chlorophenylsulfonylamino)ethylsulfinyl]-2,6-difluorophenoxylacetic acid (Compound No. 126)
m.p. 129°–129.5° C.

4-[2-(4-Chlorophenylsufonylamino)ethylsulfonyl]-2,6-difluorophenoxylacetic acid(Compound No. 127)
m.p. 163°–163.5° C.

EXAMPLE 12

To a mixture of 2,6-difluorophenol (25 g), potassium carbonate (39.5 g) and acetone (100 ml) was added dropwise with stirring at room temperature a solution of methyl bromoacetate (17.8 ml) in acetone (100 ml). After stirring at room temperature overnight, the reaction mixture was taken up in a mixture of conc. hydrochloric acid (40 ml) and ice water (500 ml), and extracted with ethyl acetate. The ethyl acetate layer was washed with a saturated aqueous sodium chloride solution and dried over anhydrous magnesium sulfate. Evaporation of the solvent under reduced pressure gave methyl 2,6-difluorophenoxyacetate (38 g) as a colorless oil.

$^1$H-NMR (CDCl$_3$) δ: 3.80(3H, s), 4.77(2H, s), 6.8–7.1(3H, m)

To a mixture of methyl 2,6-difluorophenoxyacetate (7.6 g) and methylene chloride (50 ml) was added dropwise chlorosulfonic acid (5.0 ml), and the reaction mixture was stirred at room temperature for 1.5 hours. Thionyl chloride (4.1 ml) was added to the reaction mixture, and the mixture was heated at reflux for 40 minutes. The reaction mixture, after cooling, was poured into ice water (200 ml), and the methylene chloride layer was washed successively with water and a saturated aqueous sodium chloride solution and dried over anhydrous magnesium sulfate. Evaporation of the solvent under reduced pressure gave methyl (2,6-difluoro-4-chlorosulfonyl)phenoxyacetate (11.1 g) as a colorless oil.

$^1$H-NMR (CDCl$_3$) δ: 3.80(3H, s), 4.96(2H, s), 7.63(2H, m)

To a mixture of methyl (2,6-difluoro-4-chlorosulfonyl)phenoxyacetate (11.1 g), tin (powder, 15.3 9) and methanol (100 ml) was added dropwise with stirring at 50°–60° C. conc. hydrochloric acid (25 ml), and the reaction mixture was heated at reflux with stirring for 2 hours. After cooling, the reaction mixture was poured into ice water (200 ml) with decanting the insolubles, and extracted with methylene chloride. The methylene chloride layer was washed with a saturated aqueous sodium chloride solution, and dried over anhydrous magnesium sulfate. Evaporation of the solvent under reduced pressure gave methyl (2,6-difluoro-4-mercapto)phenoxyacetate (8.0 g) as an yellow oil.

A mixture of methyl (2,6-difluoro-4-mercapto)-phenoxyacetate (8.0 g), potassium carbonate (5.6 g) and acetone (20 ml) was stirred under an argon atmosphere at room temperature for 20 minutes. To the reaction mixture was added dropwise over 10 minutes period a solution of N-(2-chloroethyl)-4-chlorophenylsulfonamide (8.9 g) in acetone (30 ml), and the mixture was stirred at room temperature overnight. The reaction solution was poured into a mixture of conc. hydrochloric acid (8 ml) and ice water (200 ml), and extracted with ethyl acetate. The ethyl acetate layer was washed successively with water and a saturated aqueous sodium chloride solution and dried over anhydrous magnesium sulfate. The solvent was evaporated under reduced pressure, the residue was recrystallized from an aqueous methanol solution to give methyl 4-[2-(4-chlorophenyl-suflonylamino)ethylthio]-2,6-difluorophenoxyacetate (Compound No. 128) (12.7 g).
m.p. 79.5°–80.5° C.

EXAMPLE 13

To a mixture of ethyl 4-[2-(4-chlorophenylsulfonylamino)ethylthio]-2,6-difluorophenoxyacetate (0.46 g) and tetrahydrofuran (30 ml) was added under ice cooling lithium aluminum hydride (38 mg), and the mixture was stirred at room temperature for an hour. To the reaction mixture was added successively 10% aqueous sodium hydroxide solution (0.2 ml), ethyl acetate (30 ml) and anhydrous sodium sulfate (1 g), and the insolubles were removed by filtration. After evaporation of the filtrate under reduced pressure, the residue was chromatographed on silica gel column (ethyl acetate:hexane=1:1), and the desired fractions were collected and recrystallized from ethyl ether/isopropyl ether mixture to give 2-{4-[2-(4-chlorophenylsulfonylamino)ethylthio]-2,6-difluorophenoxy}ethanol (Compound No. 129).
m.p. 43.5°–45° C.

EXAMPLE 14

To a mixture of 4-hydroxybenzaldehyde (6.1 g), potassium carbonate (13.8 g), sodium iodide (0.75 g) and dimethylformamide (110 ml) was added N-(ethoxycarbonylmethyl)-2-chloroacetamide (8.9 g), and the mixture was stirred at 80° C. for 30 minutes. The reaction mixture was poured into 3% hydrochloric acid and extracted with ethyl acetate. The ethyl acetate layer was washed successively with water and a saturated aqueous sodium chloride solution and dried over anhydrous magnesium sulfate. After evaporation of the solvent under reduced pressure, the residue was chromatographed on silica gel column (eluent; ethyl acetate), the desired fractions were collected and recrystallized from ethyl acetate/hexane to give N-(ethoxycarbonylmethyl)-2-(4-formylphenoxy)acetamide (4.09 g).
m.p. 94.5°–95.5° C.

To a mixture of N-(ethoxycarbonylmethyl)-2-(4-formylphenoxy)acetamide (4.6 g) and ethanol (150 ml) was added under ice cooling sodium borohydride (0.25 g), and the mixture was stirred at room temperature for 30 minutes. To the reaction mixture was added 3% hydrochloric acid, and the mixture was extracted with ethyl acetate. The ethyl acetate layer was washed with a saturated aqueous sodium chloride solution and dried over anhydrous magnesium sulfate. Evaporation of the solvent under reduced pressure gave N-(ethoxycarbonylmethyl)-2-(4-hydroxymethylphenoxy)acetamide (4.03 g).

$^1$H-NMR (CDCl$_3$) δ: 1.29(3H, t, J=7 Hz), 1.72(1H, brs), 4.10(2H, d, J=5 Hz), 4.22(2H, q, J=7 Hz), 4.51(2H, s), 4.64(2H, s), 6.92(2H, m), 7.08(1H, brs), 7.32(2H, m)

A mixture of N-(ethoxycarbonylmethyl)-2-(4-hydroxymethylphenoxy)acetamide (3.96 g), triphenylphosphine (3.88 g), carbon tetrachloride (10 ml) and methylene chloride (20 ml) was heated at reflux for 1.5 hours. The reaction mixture was evaporated under reduced pressure, and ethyl acetate was added to the residue. After removal of the insolubles by filtration, the filtrate was chromatographed on silica gel column (eluent; ethyl acetate), and the desired fractions were collected and recrystallized from ethyl acetate/ether to give N-(ethoxycarbonylmethyl)-2-(4-chloromethylphenoxy)acetamide (2.8 g).

m.p. 88.5°–90.5° C.

A mixture of N-(ethoxycarbonylmethyl)-2-(4-chloromethylphenoxy)acetamide (2.5 g), 2-(4-chlorophenylsulfonylamino)ethanethiol (3.36 g), potassium carbonate (2.5 g) and dimethylformamide (50 ml) was stirred at room temperature for 3 days. The reaction mixture was poured into 3% hydrochloric acid and extracted with ethyl acetate. The ethyl acetate layer was washed successively with water and a saturated aqueous sodium chloride solution and dried over anhydrous magnesium sulfate. After evaporation of the solvent under reduced pressure, the residue was chromatographed on silica gel column (eluent; ethyl acetate:hexane=1:2–1:0), and the desired fractions were collected and recrystallized from ether to give N-(ethoxycarbonylmethyl)-4-[2-(4-chlorophenylsulfonylamino)ethylthiomethyl]-2,6-difluorophenoxyacetamide (Compound No. 130).

m.p. 88.5°–89.5° C..

The compound obtained in Example 14 was treated with an aqueous sodium hydroxide solution to give N-(carboxymethyl)-4-[2-(4-chlorophenylsulfonylamino)ethylthiomethyl]-2,6-difluorophenoxyacetamide (Compound No. 131).

m.p. 140°–140.5° C.

EXAMPLE 15

Methyl 4-[2-(4-chlorophenylsulfonylamino)ethylthio]-2,6-difluorophenoxyacetate (1 g) was added to methanol (50 ml) saturated with ammonia gas, and the mixture was allowed to stand at room temperature for 3 days. The reaction mixture was evaporated under reduced pressure, and the residue was recrystallized from methanol to give 4-[2-(4-chlorophenylsulfonylamino)ethylthio]-2,6-difluorophenoxyacetamide (Compound No. 132).

m.p. 162°–163.5° C.

Following a similar manner to that of Example 15, there were obtained the following compounds.

N,N-Dimethyl 4-[2-(4-chlorophenylsulfonylamino)ethylthio]-2,6-difluorophenoxyacetamide (Compound No. 133)

m.p. 136.3°–137.7° C.

N-Hydroxy-4-[2-(4-chlorophenylsulfonylamino)ethylthio]-2,6-difluorophenoxyacetamide (Compound No. 134).

m.p. 132.2°–133.7° C.

4-[2-(4-Chlorophenylsulfonylamino)ethylthio]-2-fluorophenoxyacetamide (Compound No. 135)

m.p. 105.8°–107.9° C.

N,N-Dimethyl-4-[2-(4-chlorphenylsulfonylamino)ethylthio]-2-fluorophenoxyacetamide (Compound No. 136)

m.p 142.8°–144.1° C.

N-Hydroxy-4-[2- 4-chlorophenylsulfonylamino)ethylthio]-2-fluorophenoxyacetamide (Compound No. 137)

$^1$H-NMR δ: (acetone d$_6$) 2.9–3.3(4H, m), 4.73(2H, s), 6.9(1H, brs), 7.0–7.2(3H, m), 7.58(2H, d, J=8.79 Hz), 7.86(2H, d, J=8.79 Hz), 8.9(1H, brs), 10.4(1H, brs)

2-(4-Chlorophenylsulfonylamino)ethylthio]-phenylacetamide (Compound No. 138)

m.p. 195.3°–197.2° C.

4-[2-(Phenylsulfonylamino)ethylthio]-2,6-difluorophenoxyacetamide (Compound No. 139)

m.p. 117.6°–120.8° C.

N,N-Dimethyl-4-[2-(phenylsulfonylamino)ethylthio]-2,6-difluorophenoxyacetamide (Compound No. 140)

$^1$H-NMR δ: (acetone d$_6$) 2.91(3H, s), 3.0–3.2(4H, m), 3.09(3H, s), 4.91(2H, s) 6.8–7.1(2H, m), 6.9(1H, brs), 7.5–7.7(3H, m), 7.8–7.9(2H, m)

N-Hydroxy-4-[2-(phenylsulfonylamino)ethylthio]-2,6-difluorophenoxyacetamide (Compound No. 141)

$^1$H-NMR δ: (acetone d$_6$) 3.0–3.2(4H, m), 4.69(2H, s), 6.9(1H, brs), 6.9–7.1(2H, m), 7.5–7.7(3H, m), 7.8–8.0(2H, m), 8.7(1H, brs), 10.5(1H, brs)

4-[2-(Phenylsulfonylamino)ethylthio]-2-fluorophenoxyacetamide (Compound No. 142)

m.p. 108.9°–110.4° C.

N,N-Dimethyl-4-[2-(phenylsulfonylamino)ethylthio]-2-fluorophenoxyacetamide (Compound No. 143)

m.p. 104°–105.4° C.

N-Hydroxy-4-[2-(phenylsulfonylamino)ethylthio]-2-fluorophenoxyacetamide (Compound No. 144)

$^1$H-NMR δ: (acetone d$_6$) 2.9–3.4(4H, m), 4.72(2H, s), 6.8(1H, brs), 6.9–7.2(3H, m), 7.5–7.7(3H, m), 7.7–8.0(2H, m), 8.8(1H, brs), 10.5(1H, brs)

4-[2-(phenylsulfonylamino)ethylthio]phenylacetamide (Compound No. 145)

m.p. 152.8°–155.9° C.

What is claimed is:

1. A sulfonamide derivative represented by the formula $$A-SO_2NHCH_2CH_2S(CH_2)_n\underset{(O)_m}{|}-\underset{Y}{\overset{X}{\bigcirc}}-B-R$$

wherein A is a naphthyl group, a pyridyl group, a phenyl group, a phenyl group substituted by 1 to 5 members selected from the group consisting of a halogen atom, an alkyl group having 1 to 4 carbon atoms, an alkoxy group having 1 to 4 carbon atoms, a nitro group and an acetamido group, or an alkyl group having 1 to 20 carbon atoms, B is an alkylene group having 1 to 3 carbon atoms, a group of —OCH$_2$— or a group of —CH=CH—, X and Y are the same or different, and are each a hydrogen atom or a fluorine atom, R is a carboxy group, an alkyoxycarbonyl group having 2 to 5 carbon atoms, a hydroxymethyl group or a group of $$-\underset{\underset{}{\overset{O}{\|}}}{C}-N\underset{R^2}{\overset{R^1}{\diagup}}$$

(wherein $R^1$ is a hydrogen atom or an alkyl group having 1 to 3 carbon atoms, and $R^2$ is a hydrogen atom, a hydroxyl group, an alkyl group having 1 to 3 carbon atoms, a carboxymethyl group or an alkoxycarbonylmethyl group having 3 to 6 carbon atoms), m is an integer from 0 to 2, n is an integer from 0 to 3, or a salt thereof.

2. A sulfonamide derivative represented by the formula

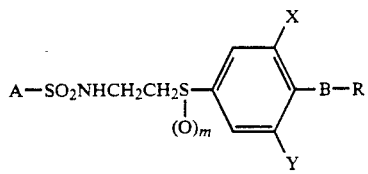

wherein A is a phenyl group substituted by 1 to 5 members selected from the group consisting of a halogen atom, an alkyl group having 1 to 4 carbon atoms, an alkoxy group having 1 to 4 carbon atoms, a nitro group and an acetamido group, B is an alkylene group having 1 to 3 carbon atoms or a group of $-OCH_2-$, X and Y are the same or different, and are each a hydrogen atom or a fluorine atom, R is a carboxy group or an alkyoxycarbonyl group having 2 to 4 carbon atoms, and m is an integer from 0 to 2, or a salt thereof.

3. A sulfonamide derivative represented by the formula 4-[2-(phenylsulfonylamino)ethylsulfonyl]phenoxyacetic acid.

* * * * *